US010456416B2

(12) United States Patent
Koller et al.

(10) Patent No.: US 10,456,416 B2
(45) Date of Patent: Oct. 29, 2019

(54) COMPOSITIONS AND METHODS OF TREATING MICROBES

(71) Applicant: Plurogen Therapeutics, LLC, Norristown, PA (US)

(72) Inventors: Neal Koller, Norristown, PA (US); George Rodeheaver, Charlottesville, VA (US); John Bistline, Jr., Drexel Hill, PA (US); Steven Coates, Broomall, PA (US)

(73) Assignee: Plurogen Therapeutics, LLC, Norristown, PA (US)

( * ) Notice: Subject to any disclaimer, the term of this patent is extended or adjusted under 35 U.S.C. 154(b) by 0 days.

(21) Appl. No.: 15/002,154

(22) Filed: Jan. 20, 2016

(65) Prior Publication Data

US 2016/0206651 A1 Jul. 21, 2016

Related U.S. Application Data

(60) Provisional application No. 62/105,569, filed on Jan. 20, 2015.

(51) Int. Cl.
| A61K 31/77 | (2006.01) |
| A61K 45/06 | (2006.01) |
| A61P 31/00 | (2006.01) |
| A61P 17/02 | (2006.01) |
| A61K 9/00 | (2006.01) |
| A61K 47/10 | (2017.01) |
| A61K 9/08 | (2006.01) |

(52) U.S. Cl.
CPC ............ *A61K 31/77* (2013.01); *A61K 9/0014* (2013.01); *A61K 9/08* (2013.01); *A61K 45/06* (2013.01); *A61K 47/10* (2013.01); *A61P 17/02* (2018.01); *A61P 31/00* (2018.01)

(58) Field of Classification Search
CPC .................................. A61K 47/10; A61K 31/77
See application file for complete search history.

(56) References Cited

U.S. PATENT DOCUMENTS

| 4,906,169 | A | 3/1990 | Chien et al. |
| 4,920,158 | A | 4/1990 | Murray et al. |
| 4,951,622 | A | 8/1990 | Takahashi et al. |
| 5,232,702 | A | 8/1993 | Pfister et al. |
| 5,284,833 | A | 2/1994 | McAnalley et al. |
| 5,298,260 | A | 3/1994 | Viegas et al. |
| 5,326,567 | A | 7/1994 | Capelli |
| 5,393,529 | A | 2/1995 | Hoffmann et al. |
| 5,399,092 | A | 3/1995 | Olsen |
| 5,470,568 | A | 11/1995 | Lee |
| 5,605,687 | A | 2/1997 | Lee |
| 5,607,683 | A | 3/1997 | Capelli |
| 5,635,540 | A | 6/1997 | Edlich et al. |
| 5,804,213 | A | 9/1998 | Rolf |
| 6,039,965 | A | 3/2000 | Donlan et al. |
| 6,096,225 | A | 8/2000 | Yang et al. |
| 6,096,324 | A | 8/2000 | Mansouri |
| 6,110,381 | A | 8/2000 | Wright |
| 6,149,822 | A | 11/2000 | Fabri et al. |
| 6,201,065 | B1 | 3/2001 | Pathak et al. |
| 6,323,219 | B1 | 11/2001 | Costanzo |
| 6,328,991 | B1 | 12/2001 | Myhling |
| 6,395,189 | B1 | 5/2002 | Fabri et al. |
| 6,399,092 | B1 | 6/2002 | Hobson et al. |
| 6,410,645 | B1 | 6/2002 | Pathak et al. |
| 6,440,437 | B1 | 8/2002 | Krzysik et al. |
| 6,585,961 | B1 | 7/2003 | Stockel |
| 6,695,823 | B1 | 2/2004 | Lina |
| 6,723,688 | B1 | 4/2004 | Malik et al. |
| 6,903,243 | B1 | 6/2005 | Burton |
| 6,927,237 | B2 | 8/2005 | Hei et al. |
| 6,977,082 | B2 | 12/2005 | Seitz, Jr. et al. |
| 6,977,083 | B1 | 12/2005 | Huebler |
| 7,083,806 | B2 | 8/2006 | Rippon et al. |
| 7,144,992 | B2 | 12/2006 | Madhyastha |
| 7,276,051 | B1 | 10/2007 | Henley |
| 7,700,819 | B2 | 4/2010 | Ambrosio |
| 7,951,100 | B2 | 5/2011 | Hunt |
| 7,976,875 | B2 | 7/2011 | Myntti |
| 8,871,248 | B2 | 10/2014 | Rodeheaver et al. |
| 8,980,243 | B2 | 3/2015 | Koller et al. |
| 9,283,278 | B2 * | 3/2016 | Rodeheaver ........... A01N 43/54 |
| 9,603,966 | B2 | 3/2017 | Rodeheaver et al. |
| 2005/0064021 | A1 | 3/2005 | Rippon et al. |
| 2005/0079147 | A1 | 4/2005 | Delaey et al. |
| 2005/0245906 | A1 | 11/2005 | Makower |
| 2005/0271604 | A1 | 12/2005 | Gestrelius et al. |
| 2006/0018945 | A1 | 1/2006 | Britigan et al. |
| 2006/0052452 | A1 | 3/2006 | Scholz |
| 2006/0246075 | A1 | 11/2006 | Mercken et al. |
| 2007/0093517 | A1 | 4/2007 | Newton |
| 2007/0219471 | A1 | 9/2007 | Johnson |
| 2007/0258996 | A1 | 11/2007 | Mookerjee et al. |
| 2008/0031831 | A1 | 2/2008 | Laali |
| 2009/0202615 | A1 | 8/2009 | Rodeheaver et al. |
| 2009/0216204 | A1 | 8/2009 | Bhavaraju |
| 2009/0226541 | A1 | 9/2009 | Scholz et al. |
| 2010/0036334 | A1 | 2/2010 | Heagle |
| 2010/0183519 | A1 * | 7/2010 | Katz ................... A61K 9/0014 424/9.2 |
| 2010/0305524 | A1 | 12/2010 | Vess |
| 2011/0251566 | A1 | 10/2011 | Zimnitsky |
| 2012/0207700 | A1 | 8/2012 | Koller et al. |
| 2013/0096518 | A1 | 4/2013 | Hall |
| 2013/0101661 | A1 | 4/2013 | Rodeheaver |
| 2015/0182554 | A1 | 7/2015 | Koller |

FOREIGN PATENT DOCUMENTS

| CA | 1297792 C | 3/1992 |
| CA | 2433082 C | 7/2002 |
| CA | 2599653 A1 | 9/2006 |
| CA | 2695151 A1 | 2/2009 |
| DE | 10238450 A1 | 3/2004 |

(Continued)

OTHER PUBLICATIONS

Yamada et al. CAS: 157: 189033, 2011.*

(Continued)

*Primary Examiner* — Rei Tsang Shiao

(74) *Attorney, Agent, or Firm* — Fitch, Even, Tabin & Flannery LLP

(57) ABSTRACT

Disclosed herein are compositions and methods to treat microbial infections and heal wounds. In some embodiments, the microbial infection may be a microbial biofilm. In some embodiments, the composition of the invention may include at least one surface active agent. The surface active agents may be anionic, cationic or non-ionic, or any combination thereof.

26 Claims, No Drawings

(56) References Cited

FOREIGN PATENT DOCUMENTS

| WO | WO 01/021195 A1 | 3/2001 |
|---|---|---|
| WO | 200185845 | 11/2001 |
| WO | WO 01/085845 A1 | 11/2001 |
| WO | WO 2004/037115 A2 | 5/2004 |
| WO | WO 2006/099359 A2 | 9/2006 |
| WO | WO 2007/087806 A1 | 8/2007 |
| WO | WO 2008/034138 A1 | 3/2008 |
| WO | WO 2008/103673 A1 | 8/2008 |
| WO | WO2008103673 * | 8/2008 |
| WO | WO 2008/154368 A2 | 12/2008 |
| WO | 2009055312 | 4/2009 |
| WO | WO2010/135449 * | 11/2010 |
| WO | WO 2010/135449 A1 | 11/2010 |
| WO | 2014167554 | 10/2014 |
| WO | 2015021319 | 2/2015 |

OTHER PUBLICATIONS

Ali et al., "Investigating the suitability of the Calgary Biofilm device for assessing the antimicrobial efficacy of new agents," 2006, *Biosource Technology* 97:1887-1893.
Baskaran et al. "Poloxamer-188 Improves Capillary Blood Flow and Tissue Viability in a cutaneous burn wound" Apr. 4, 2001, *J. of Surgical Res.* 101:58-61.
Birchenough et al. "Topical poloxamer-188 Improves Blood Flow Following Thermal Injury in Rat Mesenteric Microvasculature" May 2008, *Annals of Plastic Surgery* 60(5):584-588.
Braun Medical AG "B Braun—Infection Control, Wound Care, Instrument Preparation and Surface Disinfection" Apr. 12, 2006, SPG Media Limited, London, United Kingdom, http://www.hospitalmanagement.net/contractors/cleaning/b-braun/.
Canadian Office Action for corresponding Canadian Application No. 2,678,873 dated Jul. 27, 2015.
Ceri et al. "The Calgary Device: New Technology for the Rapid Determination of Antibiotic Susceptibilities of Bacterial Biofilms" Jun. 1999, *J. Clin. Microbio.* 37(6):1771-1776.
Ceri et al. "The MBEC Assay System: Multiple Equivalent Biofilms for Antibiotic and Biocide Susceptibility Testing" 2001, *Enzymol.* 337:377-385.
Chandra et al. "Antifungal Resistance of Candidal Biofilms Formed on Denture Acrylic in vitro" 2001, *J. Dental Research* 80(3):903-908.
Chiu et al. "Evaluation of the in vivo efficacy of topical tobramycin against *Pseudomonas* sinonasal biofilms" 2007, *J. Antimicrobial Chemotherapy* 59(6):1130-1134.
Costerton et al. "Microbial Biofilms" 1995, *Ann, Rev. Microbiol.* 49:711-745.
Effective Wound Cleansing, Mar. 2007, *The Clinical Services Journal*, Kent, United Kingdom, http://www.clinicalservicesjournal.com/Print.aspx?Story=2104.
European Examination Report dated Sep. 23, 2015 issued in corresponding European Application No. 08730165.1.
Extended European Search Report and Written Opinion dated Oct. 12, 2012 for EP 08730165.1.
Frank et al. "In Vitro Effects of Antimicrobial Agents on Planktonic and Biofilm Forms of *Staphylococcus lugdunensis* Clinical Isolates" May 2007, *Antimicrobial Agents and Chemotherapy* 51(3):888-895.
Gear et al. "A new silversulfadiazine water soluble gel" 1997, *Burns,* 23(5):387-391.
Goto et al. "In Vitro Bactericidal Activities of Beta-Lactamases, Amikacin, and Fluoroquinolones Against *Pseudomonas aeruginosa* Biofilm in Artificial Urine" 1999, *Urology* 53(5):1058-1062.
Horrocks "Prontosan Wound Irrigation and Gel: Management of Chronic Wounds" Dec. 14, 2006, *British Journal of Nursing* 15(22):1222-1228, London, United Kingdom, http://www.internurse.com/cgi-bin/go.pl/library/article.cgi?uid=22559.
International Search Report and Written Opinion dated Jul. 13, 2010, for International Application No. PCT/US2010/035440.

International Search Report and Written Opinion dated Jun. 27, 2008, for International Application No. PCT/US2008/054306.
Marsh "Plaque as a biofilm: pharmacological principles of drug delivery and action in the sub- and supragingival environment" 2003, *Oral Diseases* 9(1):16-22.
McLellan et al. "Oxygen delivery and Haemoglobin" 2004, *Continuing Education in Anaesthesia Critical Care & Pain* 4(4):123.
Melchior et al. "Comparative Assessment of the Antimicrobial Susceptibility of *Staphylococcus aureus* Isolates from Bovine Mastitis in Biofilm Versus Planktonic Culture" 2006, *J. Veterinary Medicine Series B* 53(7):326-332.
Nickel et al. "Bacterial biofilms and catheters: A key to understanding bacterial strategies in catheter-associated urinary tract infection" Sep./Oct. 1992, *Can J. Infect. Dis.* 3(5):261-267.
Nickel et al. "Tobramycin Resistance of *Pseudomonas aeruginosa* Cells Growing as a Biofilm on Urinary Catheter Material" Apr. 1985, *Antimicrob, Agents Chemother.* 27(4):619-624.
Olson et al. "Biofilm Bacteria: formation and comparative susceptibility to antibiotics" 2002, *Canadian J. Veterinary Research* 66:86-92.
Paulson "Efficacy of preoperative antimicrobial skin preparation solutions on biofilm bacteria" Mar. 2005, *AORN Journal* 81(3):503-506.
Rodeheaver et al. "Pharmacokinetics of a New Skin Wound Cleanser" Jul. 1, 1976, *American Journal of Surgery* 132(1):67-74.
Satas "Pressure Sensitive Adhesives and Adhesive Products in the U.S." 1989, in *Handbook of Pressure Sensitive Adhesive Technology, 2nd Edition,* New York: Van Nostrand Reinhold, pp. 1-23.
Sedlacek et al. "Antibiotic resistance in an in vitro subgingival biofilm model" 2007, *Oral Microbiology & Immunology* 22(5):333-339.
Supplemental European Search Report dated Jan. 23, 2013, for corresponding application EP 10778342.
Surdeau et al. "Sensitivity of bacterial biofilms and planktonic cells to a new antimicrobial agent, Oxsil® 320N" 2006, *J. Hospital Infection* 62(4):487-493.
Wesenberg-Ward et al. "Adhesion and Biofilm Formation of Candida Albicans on Native and Pluronic-treated Polystyrene" Jan. 1, 2005, *Biofilms* 2(1):63-71 (Abstract).
Yousef et al. "Inhibition of Bacterial Adherence and Biofilm on Contact Lenses" 1998, *Egypt. J. Biomed. Sci.* 1:79-94 (Abstract).
European Search Opinion dated Jan. 23, 2013, for European Application No. 10778342.
European Search Report and Written Opinion dated Feb. 1, 2017, for European Application No. 14833787.
European Search Report and Written Opinion dated May 17, 2017, for European Application No. 17160408.5.
European Search Report dated Feb. 3, 2017, for European Application No. 16202292.
International Preliminary Report of Patentability and Written Opinion of the International Searching Authority, dated Dec. 1, 2011, from counterpart foreign application PCT/US2010/035440.
International Preliminary Report of Patentability dated Jul. 25, 2017, for International Application No. PCT/US2016/014157.
International Search Report and Written Opinion dated Apr. 11, 2016, for International Application No. PCT/US2016/014157.
International Search Report and Written Opinion dated Dec. 16, 2014, for related International Application No. PCT/US2014/050212.
International Search Report and Written Opinion of the International Searching Authority, dated Jun. 27, 2008, from counterpart foreign application PCT/US2008/054306, International Filing Date Feb. 19, 2008.
Antifungal gel with improved skin penetration—contg. fenticonazole nitrate, poloxamer, ethanol and water, Derwent, XP002365156; May 14, 1990.
Martindale—The complete drug reference—Thirty-third Edition; Pharmaceutical Press, Great Britain, XP002784367; pp. 251-252.
European Written Opinion for European Patent Application No. 16740688.3, dated Oct. 16, 2018.

* cited by examiner

COMPOSITIONS AND METHODS OF TREATING MICROBES

CROSS-REFERENCE TO RELATED APPLICATION

This application claims benefit of and priority to U.S. Provisional Application No. 62/105,569 entitled "Compositions and Methods of Treating Microbes," filed Jan. 20, 2015, the contents which is incorporated herein by reference in its entirety.

BACKGROUND

The present invention is related to compositions and methods of treating microbial infections. Since antibiotics and other antimicrobial drugs first became widely used in the World War II era, they have saved countless lives and blunted serious complications of many feared diseases and infections. Over time, some bacteria have developed ways to circumvent the effects of antibiotics. Widespread use of antibiotics is thought to have spurred evolutionarily adaptations that enable bacteria to survive these powerful drugs. Other microbes such as viruses, fungi and parasites have developed resistance as well. Antimicrobial resistance provides a survival benefit to microbes and makes it harder to eliminate infections from the body. Ultimately, the increasing difficulty in fighting off microbes leads to an increased risk of acquiring infections in a hospital or other setting.

Further, bacteria and fungi form biofilms under certain conditions. When a group of bacteria or fungi accumulate on a surface and reach a particular cell density, they begin to secrete a polymeric substance that consists of polysaccharides, proteins and DNA and form a matrix in which the bacterial or fungal cells are entrenched. The multi-cellular aggregates or biofilms allow for individual bacterial or fungal cells or colonies of bacterial or fungal cells to exhibit coordinated behavior and confer upon the microorganism advantages including, for example, resistance to antibiotics and host immune systems. More specifically, biofilms are structured to allow respiration and fluid and nutrient exchange while preventing access of host immune cells such as phagocytes and preventing inhibitory or lytic concentrations of antimicrobials from reaching the microorganisms. As a result of these properties, infections that result from biofilm formation are notoriously difficult to eradicate and require the use of high concentrations of antimicrobial agents, removal of tissue, debridement of affected tissues and combination of these treatments. Therefore, there is a need to develop better compositions to treat microbial infections.

Mildly infected diabetic foot ulcer patients are currently treated with traditional wound care products because (1) no topical treatment is approved today for use in this population, (2) because clinicians refrain from using the many different available topical antibiotics because they are reported to be not completely effective and, (3) because clinicians refrain from using the more powerful systemic antibiotics (oral and IV antibiotics) at this stage of infection. While some of these patients respond to standard wound care (dressing changes and cleansing of the area), many progress rapidly to moderate to severe infections that require systemic antibiotics, and in some cases, hospitalization and limb amputation. Therefore, there is a need to develop methods and compositions to treat foot ulcers in diabetic patients.

BRIEF SUMMARY OF THE INVENTION

Disclosed herein are compositions and methods to treat microbial infections. In some embodiments, the composition of the invention may include at least one surface active agent. In some embodiments, anionic, cationic, or non-ionic surface active agents may be used individually, or in combination. In some embodiments, the surface active agent composition further includes water, a humectant, a preservative and one or more pH adjuster. In some embodiments, a composition to treat microbial biofilm may include a surface active agent at a concentration of about 45% w/w to about 55% w/w, water, a humectant, phenoxyethanol and one or more pH adjusters.

Also disclosed herein are methods to treat a biofilm. In some embodiments, the method may include contacting the microbial biofilm with surface active agent compositions described herein. In some embodiments, the method may include applying the composition to a wound. In some embodiments, the step of contacting the microbial biofilm may include administering the composition topically and in particular embodiments, administering the composition topically may be selected from administering by hand, administering by an extruder, spray delivery, applying a dressing including the composition or combinations thereof. In other embodiments, the step of contacting the microbial biofilm may include contacting tissue from the patient that is outside the patient and in still other embodiments, the step of contacting may include applying the composition to a dressing prior to applying the dressing to the patient.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only and is not intended to limit the scope of the present invention which will be limited only by the appended claims.

It must be noted that, as used herein and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by injection, infusion, or by either method in combination with other known techniques. Such combination techniques include heating, radiation and ultrasound.

A "biofilm" as used herein describes an aggregate of microorganisms that exhibit cooperative behavior such as, for example, secretion of a polymeric matrix that protects the microorganisms from attack by the host immune system.

By "biomaterial" is meant, a non-drug material that can be used to treat, enhance, or replace any tissue, organ, or function in an organism or a material that is compatible with tissue.

The term "diseased tissue," as used herein, refers to tissue or cells associated with an injury.

The term "improves" is used to convey that the present invention changes either the appearance, form, characteristics and/or the physical attributes of the tissue to which it is being provided, applied or administered. For example, eradication of the bio film would improve the indications of the injury.

The term "indication", as used herein, refers to a medical condition or symptoms associated with a medical condition, such as biofilm infection. For example, redness and swelling of tissue surrounding an injury may be an indication of subject in a diseased state.

"Optional" or "optionally" may be taken to mean that the subsequently described structure, event or circumstance may or may not occur and that the description includes instances where the event occurs and instances where it does not.

A "surface active agent" or "surfactant," as used herein, may refer to a substance that is capable of reducing the surface tension of a material.

The term "target", as used herein, refers to the material for which deactivation, rupture, disruption, or destruction is desired. For example, infectious microorganisms or biofilms may be considered undesirable material in an injured subject and may be a target for therapy.

As used herein, the term "therapeutic" means an agent utilized to treat, combat, ameliorate, prevent, or improve an unwanted condition or disease of a patient.

A "therapeutically effective amount" or "effective amount" of a composition as used herein is a predetermined amount calculated to achieve the desired effect. For example, a "therapeutically effective amount" of a composition of the invention may achieve one or more of preventing formation of a biofilm, disrupting preformed biofilm and/or enabling contact of one or more therapeutic agents with the microorganism responsible for the biofilm or enabling augmentation of the state of the tissue underlying the biofilm so as to ameliorate the disease state.

Generally speaking, the term "tissue" refers to any aggregation of similarly specialized cells which are united in the performance of a particular function. For example, skin may be considered a tissue.

The terms "treat," "treating" or "treatment" generally mean the exposure of a living organism to one or more physical, chemical or psychological entities or stimuli that may prevent, improve or ameliorate a diseased state. These terms are also meant to encompass exposing an inanimate object (e.g., biomaterial) to physical or chemical entities or stimuli that may enhance the object's capacity to alter a disease process in living organisms which is contacted by the object. For example, treating a living organism or biomaterial may include applying a composition to a surface of a living organism or biomaterial to deliver a therapeutic to the organism or biomaterial, enhance resistance to microbial infection and/or dissolve an existing microbial infections. Biomaterial treatment may encompass treating an entry site for catheters in the body of a patient which allow access of the catheter to, for example, blood vessels, body cavities, cerebrospinal space and the like. "Microbial infections" as used herein encompass all types of microbial infections including infections by biofilm forming microorganisms, established biofilms and infections by non-biofilm forming microorganisms.

Embodiments of the invention presented herein are generally directed to compositions for healing wounds. Further embodiments of the invention are directed to methods for using such compositions and materials including, for example, wound dressings, surgical equipment and syringes. Embodiments of the invention are directed to treating healing wounds on both living and non-living objects using the compositions described below. In particular embodiments, the compositions and methods can be used to treat a patient, living tissue, or biomaterial. Compositions used in such embodiments may be referred to as "pharmaceutical compositions" which generally refers to a composition that is meant for application on or in a patient, living tissue, or a biomaterial. Similar compositions, even those having the same makeup, may be useful in methods for treating microbial infections on objects that are not living or utilized in the treatment of a living being which are also encompassed by the invention.

In various embodiments, the composition of the invention may at least include at least one surface active agent. Surface active agents are well known in the art and suitable surface active agents for preparing the compositions of the invention are not limited. For example, anionic, cationic, or non-ionic surface active agents may be used individually or in combination. In some embodiments, non-ionic surface active agents based on a polyol and including alkylene oxide units such as ethylene oxide and propylene oxide may be used. Such non-ionic surface active agents include, but are not limited to, glycerol stearate/polyethylene glycol stearate co-polymers marketed under the trade name, ARLACEL' and sorbitan stearate/sugar cocoate copolymers marketed under the trade name, ARLATONE'.

In other embodiments, the surface active agent may be a polyol copolymer, such as, a poloxamer, meroxapol and poloxamine. Poloxamers are well known in the art and generally refer to a class of non-ionic di-block or tri-block copolymers having a central hydrophobic chain of polyoxypropylene flanked by hydrophilic chains of polyoxyethylene. An exemplary tri-block poloxamer may be of general formula:

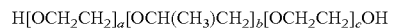

where a, b and c are independently, an integer from 1 to 1000 and reflect the number of ethylene oxide and propylene oxide monomers in each block. Poloxamers are available in various grades. The length of each polymer block may vary and may provide poloxamers with different properties. In general, poloxamers are named using three digits, the first two digits×100 give the approximate molecular mass of the polyoxypropylene core and the last digit×10 gives the percentage polyoxyethylene content in the poloxamer. For example, poloxamer 188 would be expected to contain a polyoxypropylene core of 1800 g/mol and a polyethylene content of approximately 80%. Exemplary poloxamers useful in embodiments of the invention may include, but are not limited to, poloxamers 101, 105, 105 benzoate, 108, 122, 123, 124, 181, 182, 182 dibenzoate, 183, 184, 185, 188, 212, 215, 217, 231, 234, 235, 237, 238, 282, 284, 288, 331, 333, 334, 335, 338, 401, 402, 403 and 407.

Meroxapols are well known in the art and generally refer to a class of nonionic di-block or tri-block copolymers having a central hydrophilic chain of polyoxyethylene flanked by hydrophobic chains of polyoxypropylene. An exemplary tri-block meroxapol may be of general formula:

where a, b and c are independently, an integer from 1 to 1000 and reflect the number of ethylene oxide and propylene oxide monomers in each block. Meroxapols are available in various grades. The length of each polymer block may vary and may provide meroxapols with different properties and are named using the system described above for poloxamers. Examples of meroxapols useful in embodiments of the invention include, but are not limited to, meroxapols 105, 108, 171, 172, 174, 178, 251, 252, 254, 258, 311, 312 and 314.

Poloxamines are well known in the art and generally refer to a class of nonionic tri-block copolymers having a central ethylene diamine flanked on either side by polyoxyethylene-polyoxypropylene block copolymers. Such compounds conform to general formula:

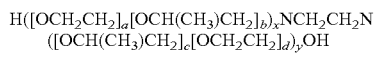

where a, b, c and d are independently, an integer from 1 to 1000 and reflect the number of ethylene oxide and propylene oxide monomers in each polyoxyethylene-polyoxypropylene copolymer block and x and y are independently, integers from 1 to 1000 and reflect the number of polyoxyethylene-polyoxypropylene copolymer blocks in each block. Poloxamines are available in different grades and are named using the system described above for poloxamers. Examples of poloxamines useful in embodiments of the invention include, but are not limited to poloxamines 304, 504, 701, 702, 704, 707, 901, 904, 908, 1101, 1102, 1104, 1301, 1302, 1304, 1307, 1501, 1502, 1504 and 1508.

The surface active agent of various embodiments may be a poloxamer, meroxapol, poloxamine or combinations thereof. In embodiments in which the surface active agent is a poloxamer, the poloxamer may be a poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 and poloxamer 407 or combinations thereof. Agent is a copolymer selected from poloxamer 127, poloxamer 188, poloxamer 237, poloxamer 335, poloxamer 407 or combinations thereof. In particular embodiments, the surface active agent may be poloxamer 188. In embodiments in which the surface active agent is a meroxapol, the meroxapol may be a meroxapol 105, meroxapol 108, meroxapol 171, meroxapol 172, meroxapol 174, meroxapol 178, meroxapol 251, meroxapol 252, meroxapol 254, meroxapol 258, meroxapol 311, meroxapol 312, meroxapol 314 or combinations thereof. In embodiments in which the surface active agent is a poloxamine, the poloxamine may be a poloxamine 304, poloxamine 504, poloxamine 701, poloxamine 702, poloxamine 704, poloxamine 707, poloxamine 901, poloxamine 904, poloxamine 908, poloxamine 1101, poloxamine 1102, poloxamine 1104, poloxamine 1301, poloxamine 1302, poloxamine 1304, poloxamine 1307, poloxamine 1501, poloxamine 1502, poloxamine 1504, poloxamine 1508 or combinations thereof.

The number average molecular weight ($M_n$) of surface active agents and particularly copolymer surface active agents of embodiments may vary and may be, for example, from about 600 to about 20,000, in some embodiments from about 600 to about 10,000, and in other embodiments, from about 1,000 to about 9,000. In particular embodiments, the $M_n$ may be from about 5,000 to about 8,500. The weight of hydrophobic groups may also vary and may be from about 45% to about 95% by weight of the copolymer.

The surface active agent of embodiments may be hydrated by mixing a suitable dry formulation of a surface active agent with a solvent such as, for example, water. Surface active agents may be hydrated by any method known in the art. For example, in some embodiments a surface active agent including a copolymer (e.g., a poloxamer) can be hydrated by cooling a mixture of the copolymer and water to an appropriate temperature such as, for example, about −10° F. to about 50° F. for at least 4 hours, about −10° F. to about 20° F. for about 8 hours, or any temperature or time period encompassed by these example ranges. The ratio of surface active agent to solvent may vary among embodiments and may be, for example, about 0.01% to about 99.99% w/w, about 20% to about 90% w/w, about 30% to about 80% w/w and about 40% to about 70% w/w. In particular embodiments the ratio of surface active agent to water may be 1:1 or about 50% w/w.

In some embodiments, the surface active agent is present in the composition at a concentration ranging from about 40% w/w to about 60% w/w, about 40% w/w to about 58% w/w, about 40% w/w to about 55% w/w, about 40% w/w to about 50% w/w, or about 40% w/w to about 4% w/w. Specific examples include about 40% w/w, about 42% w/w, about 44% w/w, about 46% w/w, about 48% w/w, about 50% w/w, about 52% w/w, about 54% w/w, about 56% w/w, about 58% w/w, or about 60% w/w.

In some embodiments, the surface active agent composition further includes water, a humectant, a preservative and one or more pH adjuster. The humectant may be, for example, glycerin and may be present at a concentration ranging from about 1% w/w to about 5% w/w, about 1% w/w to about 4% w/w, about 1% w/w to about 3% w/w, about 1% w/w to about 2% w/w, or about 1% w/w to about 1.5% w/w. In some embodiments, the preservative may be, for example, phenoxyethanol and may be present at a concentration ranging from about 0.1% w/w to about 2% w/w, about 0.1% w/w to about 1% w/w, about 0.1% w/w to about 0.8% w/w, about 0.1% w/w to about 0.5% w/w, or about 0.1% w/w to about 0.3% w/w. In some embodiments, the composition may include one or more pH adjusters, such as sodium phosphate dibasic, citric acid, or any combination thereof.

Other embodiments of compositions encompassed by the invention may include additives such as stabilizers, antioxidants, osmolality adjusting agents, buffers, pH adjusting agents, chelants, calcium chelate complexes, salts or combinations thereof. For example, in some embodiments, a stabilizer such as appropriate pharmaceutical grade surfactants such as, TWEEN or saccharides, like dextrose, may be added to the compositions of the invention and in some embodiments, such compositions may also include conventional pharmaceutical excipients and/or additives. For example, suitable pharmaceutical excipients may include stabilizers, antioxidants, osmolality adjusting agents, buffers and pH adjusting agents and suitable additives may include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or optionally, additions of calcium or sodium salts (for example, calcium chloride, calcium ascorbate, calcium gluconate or calcium lactate). Conventional nontoxic carriers may also be incorporated into such compositions and may include, for example, pharmaceutical grades of mannitol, lactose, starch, magnesium stearate, sodium saccharin, talcum, cellulose, glucose, sucrose, magnesium carbonate and the like. For example, about 1% to about 95% by volume or, in a further example, 25% to about 75% by volume of any of the carriers and excipients listed above may be mixed into the compositions of the invention. Additional additives such as coloring agents, thickeners, lubricants and so on may also be added to the compositions of the invention. Compositions of various embodiments described herein may be packaged for use as a liquid, gel, cream, solid, emulsion and dispersion.

Some embodiments are directed to compositions consisting essentially of surface active agent, water, a humectant, a preservative and one or more pH adjuster. The surface active agent is present in the composition at a concentration ranging from about 40% w/w to about 60% w/w, about 40% w/w to about 58% w/w, about 40% w/w to about 55% w/w, about 40% w/w to about 50% w/w, or about 40% w/w to about 4% w/w. Specific examples include about 40% w/w, about 42% w/w, about 44% w/w, about 46% w/w, about 48% w/w, about 50% w/w, about 52% w/w, about 54% w/w, about 56% w/w, about 58% w/w, or about 60% w/w. The humectant may be, for example, glycerin and may be present at a concentration ranging from about 1% w/w to about 5% w/w, about 1% w/w to about 4% w/w, about 1% w/w to about 3% w/w, about 1% w/w to about 2% w/w, or about 1% w/w to about 1.5% w/w. In some embodiments, the preservative may be, for example, phenoxyethanol and may be present at a concentration ranging from about 0.1% w/w to about 2% w/w, about 0.1% w/w to about 1% w/w, about 0.5% w/w to about 1% w/w, about 0.1% w/w to about 0.8% w/w, about 0.1% w/w to about 0.5% w/w, or about 0.1% w/w to about 0.3% w/w. In some embodiments, the composition may include one more pH adjusters, such as sodium phosphate dibasic, citric acid, or any combination thereof.

Some embodiments are directed to compositions consisting of surface active agent, water, a humectant, a preservative and one or more pH adjuster. The surface active agent is present in the composition at a concentration ranging from about 40% w/w to about 60% w/w, about 40% w/w to about 58% w/w, about 40% w/w to about 55% w/w, about 40% w/w to about 50% w/w, or about 40% w/w to about 45% w/w. Specific examples include about 40% w/w, about 42% w/w, about 44% w/w, about 46% w/w, about 48% w/w, about 50% w/w, about 52% w/w, about 54% w/w, about 56% w/w, about 58% w/w, or about 60% w/w. The humectant may be, for example, glycerin and may be present at a concentration ranging from about 1% w/w to about 5% w/w, about 1% w/w to about 4% w/w, about 1% w/w to about 3% w/w, about 1% w/w to about 2% w/w, or about 1% w/w to about 1.5% w/w. In some embodiments, the preservative may be, for example, phenoxyethanol and may be present at a concentration ranging from about 0.1% w/w to about 2% w/w, about 0.1% w/w to about 1% w/w, about 0.5% w/w to about 1% w/w, about 0.1% w/w to about 0.8% w/w, about 0.1% w/w to about 0.5% w/w, or about 0.1% w/w to about 0.3% w/w. In some embodiments, the composition may include one more pH adjusters, such as sodium phosphate dibasic, citric acid, or any combination thereof.

In certain embodiments, the surface active agent composition may further include one or more therapeutic agents (e.g., 2, 3, or 4 therapeutic agents may be added to a surface active agent). In general, a therapeutic agent may be added to a surface active agent after the surface active agent has been hydrated. However, in some embodiments, a dry surface active agent may be mixed with a dry therapeutic agent and the surface active agent may be hydrated following such mixing. In other embodiments, a dry mixture of surface active agent and therapeutic agent may be prepared and stored for a period of time before the surface active agent is hydrated. Any therapeutic agent known in the art may be mixed with the surface active agent to prepare a composition encompassed by the invention. For example, useful therapeutic agents may include, but are not limited to, steroids (e.g., hydrocortisone, triamcinolone), pain medications (e.g., aspirin, an NSAID and a local anesthetic), anti-inflammatory agents, antimicrobial or antibiotic agents, biological cells and biological agents of various types and combinations thereof.

Specific examples of formulations encompassed by the invention include, but are not limited to:

| | | |
|---|---|---|
| Poloxamer 188 | Surface active agent | 52.00% |
| Purified Water USP | Solvent/carrier | 44.45% |
| Glycerin USP | Humectant | 2.00% |
| Phenoxyethanol | Preservative | 1.00% |
| Na2HPO4 USP | pH adjuster | 0.36% |
| Citric Acid USP | pH adjuster | 0.19% |
| Ingredient total | | 100.0% |
| Poloxamer 188 | Surface active agent | 48.35% |
| Purified water USP | Solvent/carrier | 50.10 |
| Phenoxyethanol | Preservative | 1.00% |
| Sodium Phosphate dibasic USP | pH adjuster | 0.36% |
| Citric acid USP | pH adjuster | 0.19% |
| Ingredient total | | 100% |
| Poloxamer 188 | Surface active agent | 52.00% |
| Purified water | Solvent/carrier | 44.95% |
| Glycerin | Humectant | 2.00% |
| Phenoxyethanol | Preservative | 0.50% |
| Sodium Phosphate dibasic | pH adjuster | 0.36% |
| Citric acid | pH adjuster | 0.19% |
| Ingredient total | | 100% |

Also disclosed herein are methods to treat infection or heal damaged or wounded tissue. The methods described herein may be useful for treating patients exhibiting a number of indications or suffering from any number of conditions that may be susceptible to microbial infection or may already have a microbial infection present and/or have damaged tissue. Such patients may be considered "in need of treatment." In some embodiments, the indications or conditions that may include risk of microbial infection or may exhibit damaged tissue and may require treatment using the compositions of the invention may arise from, for example, injury in which skin and/or skin function is disrupted or surgery. Examples of such injuries may include, but are not limited to burns, abrasions, cuts, scrapes and other denuding tissue injuries or combinations of these. In other embodiments, the compositions of the invention may be used to treat chronic wounds. In general, chronic wounds are characterized by non-healing skin wounds and include, for example, chronic venous ulcers, diabetic ulcers, arterial ulcers, pressure ulcers (e.g., decubitis ulcers), radiation ulcers, traumatic wounds, open, complicated non-healing wounds and the like and combinations thereof.

In some embodiments, the method may include contacting a wound with a surface active agent compositions described above. In some embodiments, the step of contacting the microbial infection may include administering the composition topically, or applying the composition to a wound; and in particular embodiments, administering the composition topically may be selected from administering by hand, administering by an extruder, spray delivery, applying a dressing including the composition and the like or combinations thereof. In other embodiments, the step of contacting the wound may include contacting tissue from the patient that is outside the patient and in still other embodiments, the step of contacting may include applying the composition to a dressing prior to applying the dressing to the patient.

Embodiments of the invention also include methods for preventing a microbial infection on a patient by administering or applying any of the compositions described above including a surface active agent to the skin of the patient, which may or may not include a wound. Other embodiments of the invention also include a method for preventing a microbial infection on a patient including the steps of administering a composition including a surface active agent to a wound prior to infection. Yet other embodiments of the invention include a method for preventing a microbial infection on a patient including the steps of administering a composition including a surface active agent to a wound prior to infection wherein the composition is administered within 10 hours of the injury. Further embodiments of the invention include a method for treating or preventing a microbial biofilm on a patient including the steps of administering any of the compositions described above including a surface active agent to a wound.

Some embodiments include a method for preventing a microbial infection on a patient including the steps of administering a composition consisting essentially of surface active agent, water, a humectant, a preservative and one or more pH adjuster. Yet other embodiments include a method for preventing a microbial infection on a patient including the steps of administering a composition consisting essentially of surface active agent, water, a humectant, a preservative and one or more pH adjuster to a wound prior to infection wherein the composition is administered within 10 hours of the injury. Further embodiments include a method for treating or preventing a microbial infection on a patient including the steps of administering a composition consisting essentially of surface active agent, water, a humectant, a preservative and one or more pH adjuster to a wound prior to infection.

Some embodiments also include a method for preventing a microbial infection on a patient including the steps of administering a composition consisting of surface active agent, water, a humectant, a preservative and one or more pH adjuster. Yet other embodiments include a method for preventing a microbial infection on a patient including the steps of administering a composition consisting of surface active agent, water, a humectant, a preservative and one or more pH adjuster to a wound prior to infection wherein the composition is administered within 10 hours of the injury. Further embodiments include a method for treating or preventing a microbial infection on a patient including the steps of administering a composition consisting of surface active agent, water, a humectant, a preservative and one or more pH adjuster to a wound prior to infection.

Embodiments of the invention also include a dressing for treating or preventing a microbial infection or damaged tissue including a first composition layer having a surface active agent and a second composition layer having a surface active agent and a dressing material supporting said first and second composition layers. In some such embodiments, the second composition layer may be located between the first composition layer and the dressing material.

In some embodiments, the surface active agent in the first and second compositions may be the same. In other embodiments, the dressing may further include a spacer material layer between said first and second composition layers. The spacer material of such embodiments may fully or partially lose integrity upon application of the dressing to a patient. In particular embodiments, the second composition layer may impregnate the dressing material.

The compositions of embodiments of the invention may be administered in combination with secondary active agents, such as, for example, drugs, adjuvants, protease inhibitors or other compatible drugs or compounds where such combination is seen to be desirable or advantageous in achieving the desired effects of the methods described herein. In some embodiments, the secondary active agent may be administered separately from the composition and in others, the secondary active agent may be a component of the compositions of the invention. For example, in certain embodiments, the composition containing a surface active agent may further contain a drug for reducing irritation or enhancing healing such as, for example, an anti-inflammatory agent, anesthetic, pain killer or steroid.

In some such embodiments, the microbial infection may be present on a patient, for example, a human or a non-human animal and in particular embodiments, the microbial infection may be part of a wound. In other such embodiments, the infecting microorganisms may be present on a biomaterial that may contact a patient. In still other such embodiments, the infecting microorganisms may be present on tissue removed from a patient or tissue that is outside of the patient and may or may not be replaced back into the patient.

The invention also encompasses methods for using any of the compositions described above including a surface active agent for treating surfaces. Therefore, the compositions of the invention may have non-pharmaceutical applications. For example, in some embodiments, a composition including a surface active agent may be applied to an inanimate object, such as, but not limited to a chair, table, side board, machine or various parts of a machine or combinations thereof. In other embodiments, the compositions of the invention may be applied surgical instruments and/or surfaces of objects in an operating room. In still other embodiments, the compositions of the invention may be applied to surfaces of devices meant to be implanted in a patient prior to implantation such as, a medical device, for example, a catheter. In such embodiments, contacting may occur by any method known in the art. For example, in some embodiments, the composition may be applied by hand or mechanically using, for example, extrusion or spray delivery.

In embodiments in which the compositions of the invention are administered or applied directly to a tissue or biomaterial surface by hand or mechanically, it may be important to apply the composition so as to achieve a therapeutic coating. A therapeutic coating generally refers to an amount of the composition which may form a substantially uniform covering over the affected area and may encompass non-affected areas surrounding an injury or wound. In embodiments in which the composition is delivered by hand, there can be considerable variation in the thickness of layers applied by practitioners. In some embodiments, a therapeutic coating may be applied or administered alone and in other embodiments, a therapeutic coating may be applied in combination with an overlying dressing. In embodiments in which the composition is applied or administered mechanically using a device that physically pushes (i.e., extrusion) or sprays the composition onto a tissue or biomaterial surface, a uniform therapeutic coating may be achieved in a single administration or in several applications over the affected area and a therapeutic coating delivered in this manner may be provided alone or in combination with an overlying dressing.

The thickness of a therapeutic coating of the composition when applied may vary in accordance with the size of a wound, the time available to apply the composition, the amount of composition available and other variables. For example, in various embodiments, the thickness of the applied compositions may be from about 1 inch thick to less than about 1/10,000 inch thick or about 1 inch, about ½ inch, about ¼ inch, or about 1/100 inch. In some embodiments, the thickness may vary in a single application. For example, the composition may be applied more thickly in the area of a wound and less thickly in the area surrounding the wound. In other embodiments, less composition may be applied to a wound that does not exhibit signs of microbial infection while in still other embodiments, a greater amount of the composition may be applied to wounds that exhibit symptoms of microbial infection. In yet other embodiments, a wound and the area surrounding the wound may be covered with a medical fabric such as, for example, band-aids or gauze, after being contacted with the composition.

Yet other embodiments of the invention include a dressing for treating or preventing a microbial infection or treating damaged tissue that includes: a first layer including a composition containing a surface active agent; a second layer including a second composition containing a surface active agent; and a dressing material supporting the first and second composition layers. In such embodiments the second layer is located between the first layer and the dressing material. In some embodiments, the second layer may form a coating covering a surface of the dressing material and in other embodiments, the second layer is impregnated or otherwise contained within or encompassed by the dressing material. In certain embodiments, the first and second composition layers may completely encompass the dressing and in others, the first and/or second composition layers may be placed such that the compositions may be positioned to be delivered to only a portion of the patient to which the dressing is applied. For example, in one embodiment, the entire dressing includes the first and second composition layers and in another embodiment, the dressing may include a middle section that includes first and second composition layers that is flanked on either side by portions of the dressing that do not contain composition layers. In still another embodiment, the entire dressing may contain a first composition layer and a portion of the dressing may contain the second composition layer.

In still other embodiments, the dressing may further include a spacer layer between the first and second composition layers. In other embodiments, the spacer layer may be a pharmaceutical agent such as, for example, a polymer, a cream, a wax and the like that may separate the first and second compositions. In certain embodiments, the spacer layer may lose its integrity by, for example, disintegrating, dissipating, becoming porous, etc., upon application of the dressing to a patient. For example, in one embodiment, the spacer layer may degrade as it is warmed to body temperature. In general as the spacer layer loses integrity means, it may no longer function as a barrier between the first and second composition. Thus, the second composition may come into contact with patient and/or the first composition as the spacer layer loses integrity.

The dressing material of embodiment may be any pharmaceutically acceptable fabric. For example, in various embodiments, the dressing material may be gauze, a gauze pad, polymeric or natural fiber band-aid, second skin or any other type of material or fabric useful in the medical arts to cover a wound or at least keep a therapeutic agent or pharmaceutical composition in contact with a patient.

The compositions of the invention may be packaged in any way which allows a practitioner or an injured individual access to the composition following injury. For example, in one embodiment, the first and/or second compositions are contained within a tube or bottle from which the composition may be poured and applied to the injury and in another embodiment, the first and/or second composition may be absorbed onto a swab which may be used to apply the compositions of the invention. In still another embodiment, the first and/or second composition may be contained within a vial that is broken to release the composition which may then be applied by means discussed herein above. Of course, other packaging means are available and may be used in conjunction with embodiments of the invention.

Various embodiments of the invention described above may prevent microbial infection. In such embodiments, the patient or wound may not exhibit signs or symptoms of microbial infection. However, microorganisms with the potential to form a microbial infection may be present on the patient or within the wound itself. As described above, microbial infection may begin to form a biofilm only when a population of microorganisms reach a specific cell density and/or when the concentration of microorganism produced autoinducer has reached a threshold level. The concentration of autoinducer and cell density requirements may vary among biofilm forming species. Without wishing to be bound by theory, application of the compositions of the invention prior to formation of a biofilm, may reduce the microorganism population such that planktonic microorganisms may not reach an adequate cell density to form a biofilm thereby inhibiting biofilm formation.

Because microbial infections may form rapidly, it may be advantageous for emergency personnel (i.e., first responders) to apply a composition according to the present invention at the scene of the injury. Thus, in another embodiment, the present invention provides a method for treating a wounded patient by administering to the wounded patient a composition containing a surface active agent within about 10 hours of injury. In other embodiments, the wound may be treated within less than 10 hours. For example, a wound may be treated within 8 hours, within 5 hours, within 4 hours, within 3 hours, within 2 hours, within 1 hour, or within 30 minutes, within 10 minutes, or within 5 minutes. Without wishing to be bound by theory, treating an injury within about 2 hours or less may ensure that the wound is treated while the microbial infection forming pathogens in the wound are in a planktonic state or before microbial pathogens have invaded the wound. Accordingly, formation of a microbial infection may be reduced or eliminated and the wound may be more easily treated.

The present invention may be embodied in other specific forms without departing from the spirit or essential attributes thereof. This invention encompasses all combinations of the different aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

This invention and embodiments illustrating the method and materials used may be further understood by reference to the following non-limiting examples.

EXAMPLES

Example 1: Composition 1

A surface active agent composition was prepared as follows:

TABLE 1

| Poloxamer 188 | Surface active agent | 52.00% |
|---|---|---|
| Purified water | Solvent/carrier | 44.95% |
| Glycerin | Humectant | 2.00% |
| Phenoxyethanol | Preservative | 0.50% |
| Sodium Phosphate dibasic | pH adjuster | 0.36% |
| Citric acid | pH adjuster | 0.19% |
| Ingredient total | | 100% |

Example 2: Treating Diabetic Foot Ulcer by Topical Application

Composition 1 of Example 1 was applied topically on foot ulcers of 23 diabetic human subjects. Results of a 2-week clinical response is shown in Table 3. Study showed 63% clinical response (complete+partial response). No drug related adverse events were noticed.

TABLE 3

| Complete response | Partial response | Treatment failure | Unevaluable | Recurrence |
|---|---|---|---|---|
| 9 | 3 | 7 | 2 | 2 |

This study demonstrated in a large majority of patients, treatment with Composition 1 not only resulted in improvement in these mildly infected diabetic ulcers by clinical observation, but also eliminated the infecting organisms and demonstrated wound healing. The 2-week microbiologic response is shown in Table 4.

TABLE 4

| Day 3 | | | | Day 10 | | | | Day 14 | | | | 2 week F/U | | | |
|---|---|---|---|---|---|---|---|---|---|---|---|---|---|---|---|
| CR | MP | C | UE | CR | MP | C | UE | CR | MP | C | UE | CR | MP | C | R |
| 5 | 14 | 4 | 2 | 4 | 15 | 4 | | 5 | 14 | 4 | | | | | 2 |

CR: complete response;
MP: microbiologic persistence;
C: colonization;
UE: unevaluable;
R: recurrence;
F: Failure

What is claimed is:

1. A composition for treating a microbial infection consisting essentially of:
   a poloxamer at a concentration ranging from about 45 to about 55% w/w, the poloxamer consisting essentially of poloxamer 127, poloxamer 188, poloxamer 237, poloxamer 335, poloxamer 407 and combinations thereof,
   glycerin at a concentration ranging from about 1 to about 3% w/w,
   a preservative at a concentration ranging from about 0.1 to about 2% w/w,
   a pH adjuster, and
   water.

2. The composition according to claim 1, the preservative is phenoxyethanol.

3. The composition according to claim 2, the pH adjuster having at least one of citric acid and sodium phosphate dibasic.

4. The composition according to claim 3, the pH adjuster having citric acid and sodium phosphate dibasic.

5. The composition according to claim 2, the poloxamer is poloxamer 188.

6. The composition according to claim 5, the preservative is phenoxyethanol.

7. The composition according to claim 6, the pH adjuster having at least one of citric acid and sodium phosphate dibasic.

8. The composition according to claim 7, the pH adjuster having citric acid and sodium phosphate dibasic.

9. A composition for treating a microbial infection consisting essentially of:
   a poloxamer at a concentration ranging from about 45 to about 55% w/w, the poloxamer consisting essentially of poloxamer 127, poloxamer 188, poloxamer 237, poloxamer 335, poloxamer 407 and combinations thereof,
   a preservative at a concentration ranging from about 0.1 to about 2% w/w,
   a pH adjuster, and
   water.

10. The composition according to claim 9, the preservative is phenoxyethanol.

11. The composition according to claim 9, the pH adjuster having at least one of citric acid and sodium phosphate dibasic.

12. The composition according to claim 11, the pH adjuster having citric acid and sodium phosphate dibasic.

13. The composition according to claim 9, the poloxamer is poloxamer 188.

14. The composition according to claim 13, the preservative is phenoxyethanol.

15. The composition according to claim 14, the pH adjuster having at least one of citric acid and sodium phosphate dibasic.

16. The composition according to claim 15, the pH adjuster having citric acid and sodium phosphate dibasic.

17. A composition for treating a microbial infection consisting essentially of:
- a poloxamer at a concentration ranging from about 45 to about 55% w/w, the poloxamer consisting essentially of poloxamer 127, poloxamer 188, poloxamer 237, poloxamer 335, poloxamer 407 and combinations thereof,
- glycerin at a concentration ranging from about 1 to about 3% w/w,
- a preservative;
- a pH adjuster;
- a saccharide; and
- water.

18. The composition according to claim 17, the preservative is phenoxyethanol.

19. The composition according to claim 17, the pH adjuster having at least one of citric acid and sodium phosphate dibasic.

20. The composition according to claim 19, the pH adjuster having citric acid and sodium phosphate dibasic.

21. The composition according to claim 17, the poloxamer is poloxamer 188.

22. The composition according to claim 21, the preservative is phenoxyethanol.

23. The composition according to claim 22, the pH adjuster having at least one of citric acid and sodium phosphate dibasic.

24. The composition according to claim 23, the pH adjuster having citric acid and sodium phosphate dibasic.

25. The composition according to claim 24, the saccharide is sugar.

26. The composition according to claim 17, the saccharide is dextrose.

* * * * *